US00PP24196P2

(12) United States Plant Patent
Kordes

(10) Patent No.: US PP24,196 P2
(45) Date of Patent: Jan. 28, 2014

(54) CLIMBING ROSE PLANT NAMED 'KORTRAMEILO'

(50) Latin Name: *Rosa hybrida*
Varietal Denomination: KORtrameilo

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 20 days.

(21) Appl. No.: 13/507,461

(22) Filed: Jun. 29, 2012

(51) Int. Cl.
*A01H 5/00* (2006.01)

(52) U.S. Cl.
USPC ..... Plt./115

(58) Field of Classification Search
USPC ..... Plt./115
See application file for complete search history.

*Primary Examiner* — Kent L Bell

(57) ABSTRACT

A new and distinct variety of rose with long lasting, novel red flowers, and attractive foliage with excellent disease resistance. It exhibits moderately vigorous upright growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida*.

Variety denomination: The denomination of the new variety is 'KORtrameilo'.

The new variety of rose plant of the present invention originated from a controlled crossing in a breeding program of two distinct parents during the summer of 2002. The crossing was between an un-named seedling, the seed parent, and another un-named seedling, the pollen parent, from the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORtrameilo'.

CROSS REFERENCES AND FEDERAL R&D STATEMENT

There are no cross referenced or related applications. This variety was developed without the aid of any research grant.

SUMMARY OF THE INVENTION

The new rose plant may be distinguished from its seed parent, an un-named seedling, by the following combination of characteristics:

1. 'KORtrameilo' has very double medium red flowers, whereas the un-named seedling has semi-double dark red flowers.
2. 'KORtrameilo' has better disease resistance than the un-named seedling.

The new rose plant may be distinguished from its pollen parent, an un-named seedling, by the following combination of characteristics:

1. 'KORtrameilo' has large flowers and a climbing growth habit, whereas the un-named seedling has medium sized flowers and a bushy growth habit.

2. 'KORtrameilo' has excellent disease resistance, whereas the un-named seedling only has moderate disease resistance.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORtrameilo' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORtrameilo' was selected in May, 2003 from the seedling beds to be asexually propagated for further evaluation. The first asexual propagation of 'KORtrameilo' was done by budding to seedling understocks in July, 2003 at the inventor's nursery in Offenseth-Sparrieshoop, Germany.

This initial and other subsequent propagations conducted in controlled environments demonstrate that 'KORtrameilo' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, petals, leaves, prickles, and stems of 'KORtrameilo'.

DETAILED BOTANICAL DESCRIPTION

The following is a description of 'KORtrameilo', as observed growing in October, 2011 in a nursery in Jackson County, Oreg. on plants two years of age. Color references are made using The Royal Horticultural Society (London, England) Colour Chart, 2001 except where common terms of color are used.

For a comparison, several physical characteristics of the rose variety 'KORgolgat', a rose variety from the same inventor described and illustrated in U.S. Plant Pat. No. 17,376 and issued on Jan. 23, 2007 are compared to 'KORtrameilo' in Chart 1.

CHART 1

| Characteristic | 'KORtrameilo' | 'KORgolgat' |
|---|---|---|
| Bud color as sepals unfold. | Red Group 53A | Yellow Orange Group 14B |
| Petal Count. | 70 | 55-60 |
| Fragrance. | Moderate | Moderate to strong spicy fragrance |

Parents:

*Seed parent*.—Un-named seedling.

*Pollen parent*.—Un-named seedling.

Classification:

*Botanical classification*.—*Rosa hybrida*, 'KORtrameilo'.

*Commercial classification*.—Climbing rose.

FLOWER AND FLOWER BUD

Blooming habit: Recurrent.

Flower bud:

*Size*.—Upon opening, 25 mm in length from base of receptacle to end of bud and 25 mm diameter at its widest point.

*Bud form*.—Short, globular.

*Bud color*.—As sepals first unfold, bud color is Red Group 53A. When ¼ open, the upper surface of petals is Red Group 46B, and the lower surface is Red Group 53B.

*Sepals*.—Color: Upper surface: Yellow Green Group 148 C with intonations of Greyed Purple Group 184C. Lower surface: Yellow Green Group 146B with intonations of Greyed Purple Group 185B. Size: Average 20 mm (l)×5 mm (w). Shape: Sepals generally subulate. Sepal apex is generally apiculate. Weak foliaceous appendages on three of the five sepals. Base is flat at union with receptacle. Quantity: Five. Margins: Pubescent with a few stipitate glands. Surface texture: Upper side: Pubescent Lower surface: Rugose. Stipitate glands are present.

Receptacle:

*Surface*.—Smooth with light pubescence.

*Color*.—Yellow Green Group 144B.

*Shape*.—Funnel.

*Size*.—8 mm (h)×6 mm (w).

Peduncle:

*Surface*.—Smooth with fine hairs and stipitate glands.

*Length*.—45-60 mm average length.

*Diameter*.—2-3 mm average diameter.

*Color*.—Yellow Green Group 144A with intonations of Greyed Purple Group 182A.

*Strength*.—Strong.

*Borne*.—Multiple flower buds per stem, generally 1 to 5.

Flower bloom:

*Fragrance*.—Moderate.

*Duration*.—On the plant 3 to 6 days. Flowers do not drop from plant. As a cut flower, 3 to 5 days.

*Size*.—Medium flowered garden rose. When open, the average flower diameter is 80 mm and the average flower height is 40 mm.

*Form*.—Shape of flower when viewed from the side: Upon opening, upper part: Flat. Upon opening, lower part: Concave. Open flower, upper part: Flat. Open flower, lower part: Flattened convex.

Color:

*Upon opening, petals*.—Outermost petals: Outer Side: Red Group 46B. Inner Side: Red Group 46B. Innermost petals: Outer Side: Red Group 46B. Inner Side: Red Group 46B.

*Upon opening, basal petal spots*.—Basal petal spot, outermost petals: Outer Side: No distinctive coloration at petal base observed. Inner Side: White Group 155A. Basal petal spot, innermost petals: Outer Side: Green-White Group 157B. Inner Side: Green-White Group 157B.

*After opening, petals*.—Outermost petals: Outer Side: Red Group 53D. Inner Side: Red Group 53D. Innermost petals: Outer Side: Red Group 53D. Inner Side: Red Group 53D.

*After opening, basal petal spots*.—Basal petal spot, outermost petals: Outer Side: White Group 155D. Inner Side: White Group 155B. Basal petal spot, innermost petals: Outer Side: White Group 155B. Inner Side: White Group 155D.

General tonality: On open flower Red Group 53B No change in the general tonality at the end of the fourth day. Afterwards, general tonality is Red-Purple Group 71B.

Petals:

*Petal count*.—Very Double.

*Average range*.—Approximately 70 petals under normal conditions.

*Petal reflex*.—Petals reflex slightly.

*Petal edge*.—With point in center of margin.

*Petal shape*.—Obtuse. Apex shape is round. Shape of base is cuneate.

*Petal size*.—25-40 mm (l)×15-30 mm (w).

*Thickness*.—Average.

*Petal arrangement*.—Quartered nostalgic cupped.

Petaloids:

*Petaloid count*.—Average of 5-10 per flower.

*Petaloid size*.—Petaloids are 15 mm (l)×10 mm (w).

*Petaloid color*.—Color of inner side is Red Group 53B. Color of outer side is Red Group 53B.

*Petaloid margins*.—Undulated, with point in center of margin.

*Petaloid shape*.—Spatulate with a point in center of margin. Apex: obtuse. Base: attenuate.

Reproductive organs:

*Pistils*.—Abundant. Approximately 45 present. Stigmas: Location: Slightly superior in position to anthers. Color: Yellow-White Group 158A. Styles: Length: About 7 mm long. Color: Greyed-White Group 157B. Intonations of Red Group 54A at the apex.

*Stamens*.—Approximately 50 on average and regularly arranged. Anthers: Size: Average 1 mm long. Pollen:

Generally present. Color: Greyed-Orange Group 164C. Filaments: Color: Red Group 50C. Length: 5 mm.

THE PLANT

Growth: Moderately Vigorous.

Plant habit: Upright, climbing habit. When grown as a budded field grown plant, the average plant height is 200 cm and the average plant width is 100 cm.

Blooming: Floriferous.

Stems:

*Stem color*.—Young wood: Yellow-Green Group 145A. Intonations: Greyed-Purple 183C. Older wood: Yellow-Green Group 144A.

*Stem surface*.—Young wood: Smooth. Older wood: Smooth.

Prickles: Present.

*Incidence*.—6 per 10 cm of stem.

*Size*.—Average length: 7 mm.

*Color*.—Immature prickles: Greyed-Red Group 182A. Mature prickles: Greyed-Orange Group 177D.

*Shape*.—Deeply concave.

*Anthocyanin*.—Color. Greyed-Purple Group 185A on immature prickles.

Leaves and leaflets: Normally 7 leaflets on normal leaves in the middle of a stem.

*Venation pattern*.—Pyramidal net pattern.

*Leaf size*.—140 mm (l)×95 mm (w).

*Abundance*.—Abundant.

*Texture*.—Leathery. Upper side of leaflet: Semi glossy. Under side of leaflet: Matte.

*Color, mature foliage*.—Upper Leaf Surface: Yellow-Green Group 147A. Lower Leaf Surface: Yellow-Green Group 147B.

*Color, juvenile foliage*.—Upper Leaf Surface: Yellow-Green Group 147B. Lower Leaf Surface: Yellow-Green Group 147B.

*Anthocyanin intonation*.—Intonations present on juvenile leaf margins, and developing leaves, of Greyed-Purple Group 183C.

Stipules:

*Size*.—15 mm long between the tips of the stipule. Main body of stipule is 5 mm in width.

*Stipule color*.—Yellow-Green Group 144B.

*Anthocyanin*.—Present along the mid-rib of upper side. Color: Greyed-Purple Group 183A.

*Margins*.—Stipitate glands present on margins.

*Shape*.—Base: Winged. Apex: Apiculate.

Petiole:

*Length*.—Average 10 mm.

*Diameter*.—Average 2 mm.

*Petiole color*.—Yellow-Green Group 146B.

*Underneath*.—A few small prickles underneath.

*Margins*.—With stipitate glands.

*Anthocyanin*.—Present along mid-rib of upper side. Greyed-Purple Group 183D.

Petiole rachis:

*Length*.—Average 20 mm.

*Diameter*.—Average 1.5 to 2.0 mm.

*Color*.—Yellow-Green Group 146C. Anthocyanin present on upper side. Greyed-Purple Group 183B.

Leaflets:

*Size*.—Average size of the terminal leaflet is 55 mm (l)×35 mm (w).

*Shape*.—Ovate. Base: Obovate. Apex: Acute.

*Margins*.—Serrated.

*Surface*.—Upper: Semi-glossy. Lower: Matte.

*Texture*.—Leathery.

*Arrangement*.—Odd pinnate.

*Venation*.—Reticulate.

Hips/seed formation: None observed.

Winter hardiness: To date, the variety has been grown successfully in USDA zones 6 to 9.

Disease resistance: Above average resistance to Powdery mildew (*Sphaerotheca pannosa*), rust (*P. disciflorum*), blackspot (*Diplocarpon rosae*), and Botrytis (*Botrytis cinerea*) diseases under normal growing conditions.

I claim:

1. A new and distinct variety of rose plant, as described and illustrated herein.

* * * * *

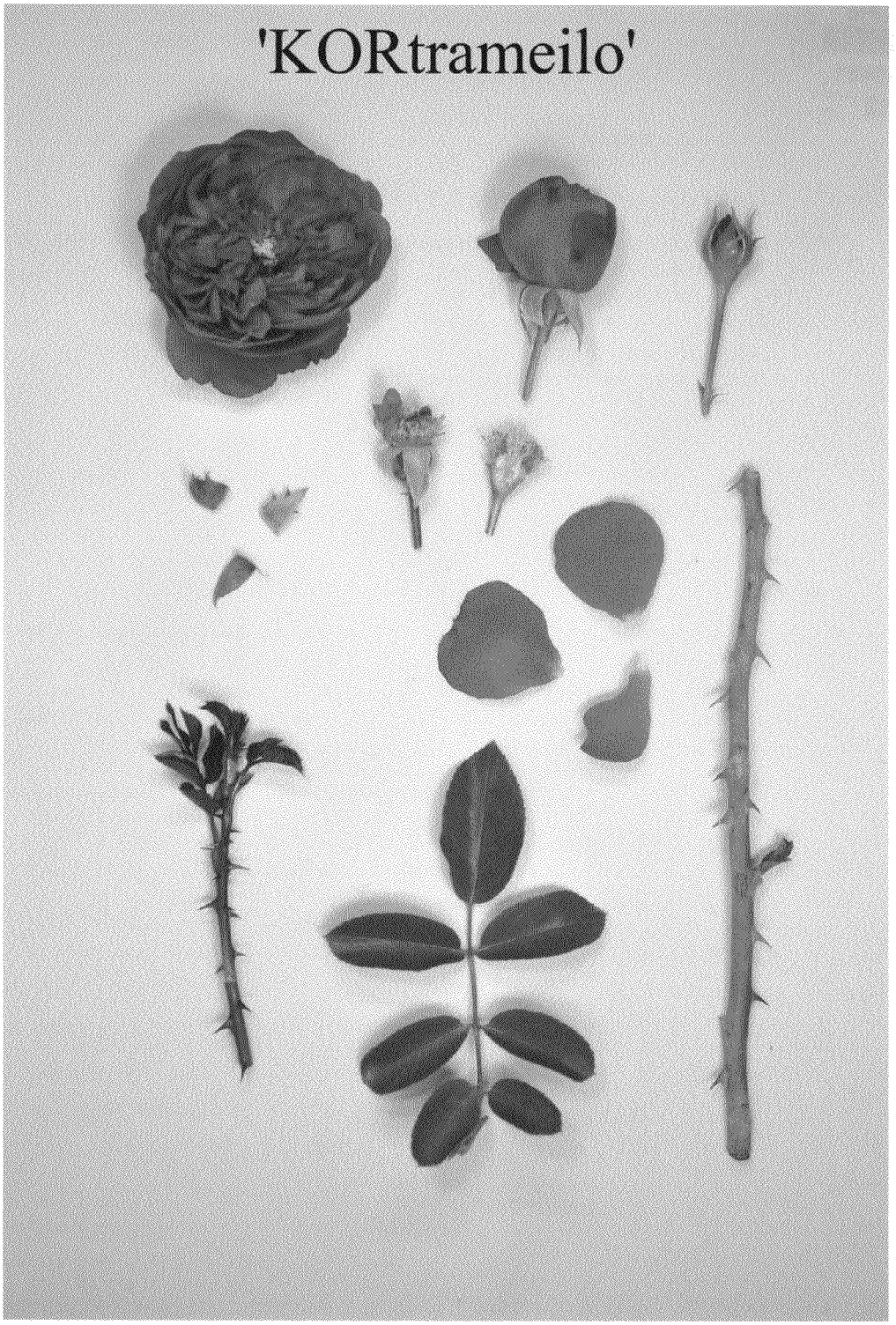
'KORtrameilo'